United States Patent [19]

Rempfler et al.

[11] 4,391,628

[45] Jul. 5, 1983

[54] 2-[4-(6-HALOQUINOXALINYL-2-OXY)-PHENOXY]PROPIONIC ACID ESTERS

[75] Inventors: Hermann Rempfler, Ettingen; Beat Böhner, Binningen, both of Switzerland

[73] Assignee: Ciba-Geigy Corporation, Ardsley, N.Y.

[21] Appl. No.: 346,359

[22] Filed: Feb. 5, 1982

[30] Foreign Application Priority Data

Feb. 16, 1981 [CH] Switzerland .................. 1009/81

[51] Int. Cl.³ .......... C07D 241/44; C07D 241/52; A 01 N 43/60
[52] U.S. Cl. ...................... 71/92; 544/353; 544/354; A01N/43/60
[58] Field of Search ............... 544/354; 71/92
[56] References Cited

U.S. PATENT DOCUMENTS 4,358,307  11/1982  Serban et al. .................. 544/354

FOREIGN PATENT DOCUMENTS 23785    2/1981  European Pat. Off. .
46468    3/1982  European Pat. Off. ............ 544/354
2609461  9/1977  Fed. Rep. of Germany .
3004770  8/1980  Fed. Rep. of Germany .
56-16475 2/1981  Japan .................. 544/354
622170   3/1981  Switzerland .
966818   8/1964  United Kingdom .......... 544/354

*Primary Examiner*—Donald G. Daus
*Assistant Examiner*—James H. Turnipseed
*Attorney, Agent, or Firm*—Frederick H. Rabin

[57] ABSTRACT

The invention relates to novel 2-[4-(6-haloquinoxalinyl-2-oxy)phenoxy]propionates with herbicidal and plant growth regulating properties and having good selectivity in different crops of cultivated plants. The novel compounds have the general formula I

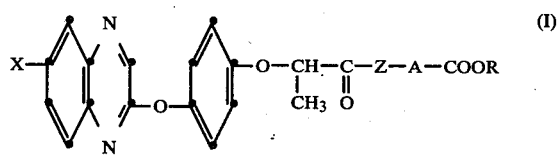

wherein X is fluorine, chlorine or bromine, Z is oxygen or sulfur, A is a $C_1$-$C_4$alkylene bridge which is unsubstituted or substituted by methyl or ethyl, and R is $C_1$-$C_4$alkyl.

19 Claims, No Drawings

2-[4-(6-HALOQUINOXALINYL-2-OXY)PHENOXY]-PROPIONIC ACID ESTERS

The present invention relates to novel esters of 2-[4-(6-haloquinoxalinyl-2-oxy)phenoxy]propionic acid having herbicidal and plant growth regulating properties, to the production thereof, and also to compositions containing them as active ingredients, as well as to the use of these novel compounds and of compositions containing them for the selective control of weeds in crops of useful plants and for regulating plant growth.

In recent years, numerous derivatives of parasubstituted phenoxypropionic acids with herbicidal properties have been disclosed, in which connection reference may be made e.g. to the following publications: German Offenlegungsschrift specifications Nos. 2 609 461, 3 004 770, European patent application No 23 785 and Swiss Pat. No. 622 170. Such compounds have been proposed as herbicides and used in actual practice for facilitating agricultural work and for improving the productivity of useful plants in agriculture and in horticulture.

However, there still exists a need to final novel herbicides with superior herbicidal properties. Herbicides which are used for agricultural and horticultural purposes are preferably compounds wich selectively control the target weeds at low rates of application without being toxic to the useful plants. Known herbicides do not always have these benefical properties.

Surprisingly, it has now been found that the novel compounds of this invention are superior in selective weed control to the products introduced onto the market and to the structurally most closely related compounds of the patent literature and, in addition, have plant growth regulating properties.

The 2-[4-(6-haloquinoxalinyl-2-oxy)phenoxy]propionic acid esters of the present invention have the general formula I

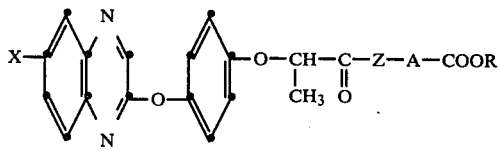

wherein X is fluorine, chlorine or bromine, Z is oxygen or sulfur, A is a $C_1$–$C_4$alkylene bridge which is unsubstituted or substituted by methyl or ethyl, and R is $C_1$–$C_4$alkyl.

Alkyl in the above definition denotes methyl, ethyl, n-propyl, isopropyl as well as butyl and the isomers thereof. An alkylene bridge is e.g. methylene, ethylene, propylene and butylene.

Preferred for their activity are compounds of the formula I, wherein (a) X is fluorine or chlorine, and (b) A is a $C_1$–$C_4$ alkylene bridge which is unsubstituted or substituted by methyl or ethyl and which contains altogether at most 3 carbon atoms.

Particularly preferred are compounds of the formula I, wherein X is fluorine or chlorine and A is a $C_1$–$C_4$alkylene bridge which is unsubstituted or substituted by methyl or ethyl and which contains altogether at most 3 carbon atoms.

As preferred individual compounds there may be mentioned:

methoxycarbonylmethyl 2-[4-(6-chloroquinoxalinyl-2-oxy)-phenoxy]thiopropionate, ethoxycarbonylmethyl 2-[4-(6-fluoroquinoxalinyl-2-oxy)-phenoxy]propionate, methoxycarbonylmethyl 2-[4-(6-fluoroquinoxalinyl-2-oxy)-phenoxy]thiopropionate, 1-(methoxycarbonyl)ethyl 2-[4-(6-fluoroquinoxalinyl-2-oxy)-phenoxy]propionate, n-butoxycarbonylmethyl 2-[4-(6-fluoroquinoxalinyl-2-oxy)-phenoxy]thiopropionate, 1-(ethoxycarbonyl)-n-propyl 2-[4-(6-chloroquinoxalinyl-2-oxy)phenoxy]propionate, and 1-(n-butoxycarbonyl)ethyl 2-[4-(6-chloroquinoxalinyl-2-oxy)phenoxy]propionate.

The novel esters of formula I are obtained by methods which are known per se.

A first process for obtaining the compounds of the invention comprises reacting an acid halide of the formula II

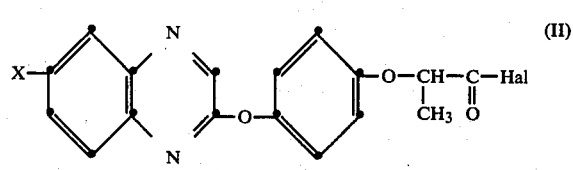

wherein X is as defined for formula I and Hal is chlorine or bromine, optionally in an organic solvent and optionally in the presence of a base, with an alkane-carboxylic acid ester of the formula III

wherein A, R and Z are as defined for formula I.

A second process for obtaining the compounds of formula I comprises reacting a quinoxalinyl chloride of the formula IV

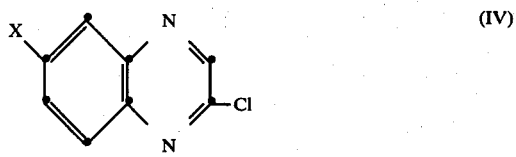

wherein X is as defined for formula I, in an inert solvent and optionally in the presence of a base, with a phenoxy-propionic acid ester of the formula V

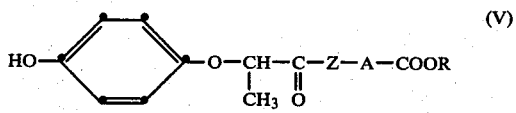

wherein A, R and Z are as defined for formula I.

A third process for obtaining the compounds of formula I comprises reacting a quinoxalinyl-2-oxy phenol of the formula VI

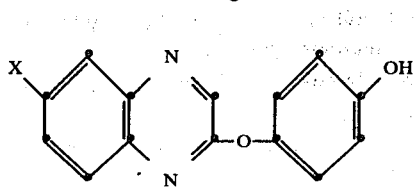

wherein X is as defined for formula I, in an inert solvent and optionally in the presence of a base, with a propionic acid ester of the formula VII

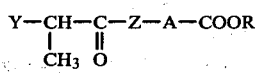

wherein A, R and Z are as defined for formula I and Y is a leaving group.

Suitable inert solvents for the first process are: ethers such as diethyl ether, tetrahydrofuran, dimethoxyethane or dioxan, and hydrocarbons such as hexane, cyclohexane, benzene, toluene, xylene or petroleum fractions such as petroleum ether or ligroin. Suitable organic solvents for the two last mentioned processes are polar aprotic solvents. Examples of such solvents are: ketones such as acetone or methyl ethyl ketone, amides such as N,N-dimethyl formamide, hexamethylphosphoric triamide or N-methylpyrrolidone, acetonitrile or dimethyl sulfoxide.

Examples of bases for the first process are tertiary amines such as triethylamine, pyridine or 4-dimethylaminopyridine, carbonates such as sodium or potassium carbonate, bicarbonates such as sodium or potassium bicarbonate, and oxides such as calcium or magnesium oxide. Suitable bases for the two last mentioned processes are: alcoholates such as sodium methylate, sodium ethylate or potassium tertbutylate, hydrides such as sodium or calcium hydride, hydroxides such as sodium or potassium hydroxide, and carbonates such as sodium or potassium carbonate.

Examples of suitable leaving groups are halogens, preferably chlorine, bromine and iodine, with bromine and iodine being preferred; or sulfonic acid radicals, such as those of toluenesulfonic acid, 4-bromobenzenesulfonic acid, methanesulfonic acid or trifluoromethanesulfonic acid.

The reaction temperatures for all three processes are in the range from −20° to +170° C., with the preferred range being from 10° C. to the boiling point of the reaction mixture.

Some of the starting compounds of the formulae III, IV, V, VI and VII are known and commercially available, or they can be easily prepared by methods analogous to known ones.

The starting compounds of the formula II can be obtained by the following reaction sequence: alkyl esters of 2-[4-(6-haloquinoxalinyl-2-oxy)phenoxy]propionic acid are hydrolysed to the free acids and these are converted by methods which are known per se, e.g. by reaction with $SOBr_2$, $POCl_3$, $PCl_3$, $PBr$, $PCl$, to the acid halides of the formula II.

The compounds of formula I have selective herbicidal properties. They are particularly suitable for controlling monocot weeds in crops of useful dicot plants such as soybeans, sugar beet, cotton and different types of vegetables, without damaging the useful plants or only causing damage to them at higher rates of application. The compounds are applied direct to the plants or seeds thereof, or to the locus of the plants, in a herbicidally effective amount.

In addition, the compounds of formula I have plant growth regulating properties. It is therefore possible to influence the growth of plants favourably. The different ways in which plants may be influenced can be summarised as follows: Growth inhibition of e.g. grass in parks or on embankments; growth inhibition e.g. of cereals to increase resistance to atmospheric influences; growth inhibition of e.g. weeds so that they do not compete with useful plants:, inhibition of germination of e.g. storage potatoes or seeds; promotion of e.g. blossoming or fruit setting in fruit or ornamental flowers; advancement of ripening of e.g. fruit in order to synchronise the time of harvesting; promotion of root growth of e.g. cereals or vegetables in order to improve resistance to lodging and/or the food intake of plants; or the inhibition of side-shoots or inflorescences of e.g. tobacco plants in order to increase the number of leaves.

The compounds of formula I are particularly suitable for promoting root growth. In particular, the root growth of cereal plants such as rye, barley, wheat and maize is stimulated when these plants are treated with small amounts of the compounds. In general, the rates of application are below those which produce a herbicidal effect. In addition, it is advantageous to apply the compounds of formula I direct to the soil to promote growth, or else to treat seeds with the compounds before sowing (seed dressing).

The invention also relates to herbicidal and plant growth regulating compositions which contain a novel compound of the formula I and also to methods of controlling weeds pre- and postemergence, especially monocot grasses, and to methods of influencing plant growth, especially of promoting root growth.

The compounds of the formula I are used in unmodified form or preferably together with the adjuvants conventionally employed in the art of formulation, and are therefore formulated in known manner to emulsifiable concentrates, directly sprayable or dilutable solutions, dilute emulsions, wettable powders, soluble powders, dusts, granulates, and also encapsulations in e.g. polmyer substances. Just like the nature of the compositions, the methods of application, such as spraying, atomising, dusting, scattering or pouring, are chosen in accordance with the intended objectives and the prevailing circumstances.

The formulations, i.e. the compositions or preparations containing the compound (active ingredient) of the formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane, or paraffins, alcohols and glycols and their ethers and esters, such as ethanol, ethylene glycol, ethylene glycol monomethyl or monoethyl ether; ketones such as cyclohexanone, strongly polar solvents such as N-methyl-2-pyrrolidone, dimethyl sulfoxide or dimethyl formamide; as wel as epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers or materials such as calcite or sand. In addition, a great number of pregranulated materials of inorganic or organic nature can be used, e.g. especially dolomite or pulverised plant residues.

Depending on the nature of the compound of formula I to be formulated, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali, alkaline earth or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali salts, alkaline earth salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminepolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 glycol units per propylene glycol unit.

Representative examples of non-ionic surfactants are nonylphenol-polyethoxyethanols, castor oil polyglycol ethers, polypropylene/polyethylene oxide adducts, tributylphenoxypolyethoxyethanol, polyethylene glycol and octylphenoxypolyethoxyethanol. Fatty acid esters of polyoxyethylene sorbitan and polyoxyethylene sorbitan trioleate are also suitable non-ionic surfactants.

Cationic surfactants are preferably quaternary ammonium salts which contain, as N-substituent, at least one polyglycol ether or $C_8$–$C_{22}$alkyl radical and, as further substituents, lower unsubstituted or halogenated alkyl, benzyl or lower hydroxyalkyl radicals. The salts are preferably in the form of halides, methylsulfates or ethylsulfates, e.g. stearyltrimethylammonium chloride or benzyl di-(2-chloroethyl)ethylammoniuum bromide.

The surfactants customarily employed in the art of formulation are described e.g. in the following publications: "McCutcheon's Detergents and Emulsifiers Annual", MC Publishing Corp., Ringwood, New Jersey, 1979; Sisely and Wood, "Encyclopedia of Surface Active Agents", Chemical Publishing Co. Inc., New York, 1964.

The pesticidal formulations will normally contain 0.1 to 99%, preferably 0.1 to 95%, of a compound of the formula I, 1 to 99% of a solid or liquid adjuvant, and 0 to 25%, preferably 0.1 to 25%, of a surfactant.

Preferred formulations are composed in particular of the following constituents (%=percentage by weight):

Solutions active ingredient: 5 to 95%, preferably 10 to 80%
solvent: 95 to 5%, preferably 90 to 0%
surfactants: 1 to 30%, preferably 2 to 20%

Emulsifiable concentrates active ingredient: 10 to 50%, preferably 10 to 40%
surfactant: 5 to 30%, preferably 10 to 20%
liquid carrier: 20 to 95%. preferably 40 to 80%

Dusts active ingredient: 0.5 to 10%, preferably 2 to 8%
solid carrier: 99.5 to 90%, preferably 98 to 92%

Suspension concentrates active ingredient: 5 to 75%, preferably 10 to 50%
water: 94 to 25%, preferably 90 to 30%
surfactant: 1 to 40%, preferably 2 to 30%

Wettable powders active ingredient: 5 to 90%, preferably 10 to 80%, and most preferably, 20 to 60%,
surfactant: 0.5 to 20%, preferably 1 to 15%
solid carrier: 5 to 90%, preferably 30 to 70%

Granulates active ingredient: 0.5 to 30%, preferably 3 to 15%
solid carrier: 99.5 to 70%, preferably 97 to 85%.

Whereas commercial products will be preferably formulated as concentrates, the end user will normally employ dilute formulations. The formulations can be diluted to a concentration as low as 0.001%. The rates of application are normally 0.1 to 10 kg a.i./ha, preferably 0.25 to 5 kg a.i./ha.

The compositions can also contain further ingredients such as stabilisers, antifoams, viscosity regulators, binders, adhesives, as well as fertilisers or other active compounds, in order to attain special effects.

The following Examples illustrate the invention. Pressures are given in millibars (mbar).

PREPARATORY EXAMPLES

Example 1:

(a) Preparation of an intermediate

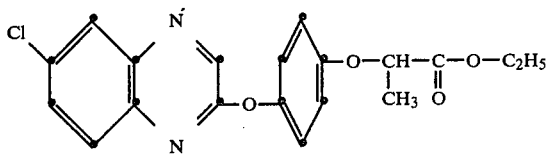

ethyl 2-[4-(6-chloroquinoxalinyl-2-oxy)phenoxy]propionate

A mixture of 24 g of 2,6-dichloroquinoxaline, 28 g of ethyl 2-(4-hydroxyphenoxy)propionate and 24.8 g of potassium carbonate are heated under reflux for 12 hours in 400 ml of methyl ethyl ketone. The salts formed are removed, the solution is concentrated, and the residue is crystallised from diethyl ether, affording 40 g of ethyl 2-[4-(6-chloroquinoxalinyl-2-oxy)phenoxy]propionate with a melting point of 90°–93° C.

(b) Preparation of a further intermediate

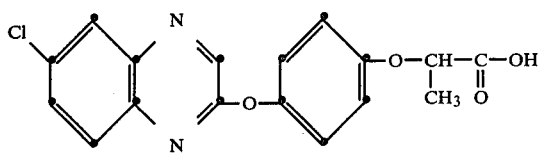

2-[4-(6-chloroquinoxalinyl-2-oxy)phenoxy]propionic acid 37.3 g of ethyl 2-[4-(6-chloroquinoxalinyl-2-oxy)phenoxy]-propionate are refluxed for 2 hours in a mixture of 50 ml of ethanol and 70 ml of aqueous 2 N sodium hydroxide solution. The reaction mixture is filtered and concentrated and the filtrate is acidified with 32% hydrochloric acid and extracted with chloroform. The chloroform phase is concentrated to give 26.8 g of 2-[4-(6-chloroquinoxalinyl-2-oxy)phenoxy]propionic acid with a melting point of 131°–133° C.

(c) Preparation of a further intermediate

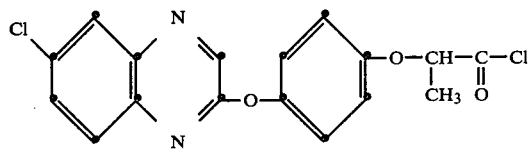

2-[4-(6-chloroquinoxalinyl-2-oxy)phenoxy]propionyl chloride 17.2 g of 2-[4-(6-chloroquinoxalinyl-2-oxy)phenoxy]-propionic acid and 10 ml of thionyl chloride are heated together for 8 hours to 60° C. Excess thionyl choride is then stripped off in vacuo and the residue is taken up in toluene in order to remove any traces of toluene still remaining and the solution is concentrated. The crude oily 2-[4-(6-chloroquinoxalinyl-2-oxy)phenoxy]propionyl chloride can be used direct for obtaining corresponding esters.

(d) Preparation of a final product

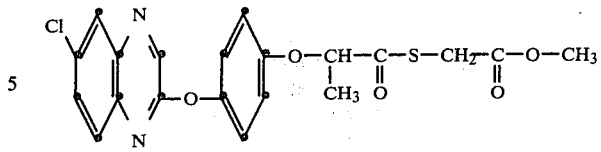

methoxycarbonylmethyl 2-[4-(6-chloroquinoxalinyl-2-oxy)phenoxy]thiopropionate

To a solution of 3.6 g of 2-[4-(6-chloroquinoxalinyl-2-oxy)phenoxy]propionyl chloride in 50 ml of toluene are added, in succession, 1.2 g of methyl thioglycolate and 1.2 g of triethylamine. The reaction mixture is stirred for 2 hours and the precipitate is then removed and the filtrate is washed with 5% hydrochloric acid, dried and concentrated. Yield: 2.6 g of methoxycarbonylmethyl 2-[4-(6-chloroquinoxalinyl-2-oxy)phenoxy]thiopropionate in the form of a brown resin which crystallises on trituration with ether. Melting point: 86°–88° C.

Table 1 lists the compounds of the formula I obtained in accordance with this Example as well as further compounds which are obtained in similar manner.

TABLE 1

| | Compounds of formula I | | | | |
|---|---|---|---|---|---|
| No. | X | Z | A | R | Physical data |
| 1 | Cl | S | —CH$_2$—CH$_2$— | CH$_3$ | |
| 2 | Cl | O | —CH$_2$—CH$_2$— | C$_2$H$_5$ | |
| 3 | Cl | S | —CH$_2$— | CH$_3$ | m.p. 86–88° C. |
| 4 | Cl | O | —CH$_2$— | CH$_3$ | |
| 5 | Cl | O | —CH(CH$_3$)— | n-C$_4$H$_9$ | n$_D^{30}$:1.5570 |
| 6 | Cl | S | —CH(CH$_3$)— | CH$_3$ | |
| 7 | Cl | O | —CH(C$_2$H$_5$)— | C$_2$H$_5$ | n$_D^{25}$:1.5675 |
| 8 | F | O | —CH$_2$— | C$_2$H$_5$ | m.p. 88–90° C. |
| 9 | F | S | —CH$_2$— | CH$_3$ | m.p. 97–99° C. |
| 10 | F | O | —CH(CH$_3$)— | CH$_3$ | n$_D^{30}$:1.5540 |
| 11 | F | S | —CH(CH$_3$)— | CH$_3$ | |
| 12 | Cl | S | —CH$_2$— | C$_2$H$_5$ | m.p. 84–86° C. |
| 13 | F | S | —CH$_2$— | C$_2$H$_5$ | m.p. 92–95° C. |
| 14 | F | S | —CH$_2$— | n-C$_4$H$_9$ | n$_D^{25}$:1.5690 |

FORMULATION EXAMPLES

Example 2

Formulation Examples for liquid active ingredients of the formula I (throughout, percentages are by weight)

| (a) Emulsifiable concentrates | (a) | (b) | (c) |
|---|---|---|---|
| active ingredient | 20% | 40% | 50% |
| calcium dodecylbenzenesulfonate | 5% | 8% | 5.8% |
| castor oil polyethylene glycol ether (36 moles of ethylene oxide) | 5% | — | — |
| tributylphenol polyethylene glycol ether (30 moles of ethylene oxide) | — | 12% | 4.2% |
| cyclohexane | — | 15% | 20% |
| xylene mixture | 70% | 25% | 20% |

Emulsions of any required concentration can be produced from such concentrates by dilution with water.

| (b) Solutions | (a) | (b) | (c) | (d) |
|---|---|---|---|---|
| active ingredient | 80% | 10% | 5% | 95% |
| ethylene glycol monomethyl ether | 20% | — | — | — |
| polyethylene glycol 400 | — | 70% | — | — |
| N—methyl-2-pyrrolidone | — | 20% | — | — |
| epoxidised coconut oil | — | — | 1% | 5% |
| ligroin (boiling range 160-190°) | — | — | 94% | — |

These solutions are suitable for application in the form of microdrops.

| (c) Granulates | (a) | (b) |
|---|---|---|
| active ingredient | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| (d) Dusts | (a) | (b) |
|---|---|---|
| active ingredient | 2% | 5% |
| highly dispersed silicic acid | 1% | 5% |
| talcum | 97% | — |
| kaolin | — | 90% |

Dusts which are ready for use are obtained by intimately mixing the carriers with the active ingredient.

Example 3

Formulation examples for solid active ingredients of the formula I (throughout, percentages are by weight)

| (a) Wettable powders | (a) | (b) |
|---|---|---|
| active ingredient | 20% | 60% |
| sodium lignosulfonate | 5% | 5% |
| sodium laurylsulfate | 3% | — |
| sodium diisobutylnaphthalene-sulfonate | — | 6% |
| octylphenol polyethylene glycol ether (7-8 moles of ethylene oxide) | — | 2% |
| highly dispersed silicic acid | 5% | 27% |
| kaolin | 67% | — |

The active ingredient is thoroughly mixed with the adjuvants and the mixture is thoroughly ground in a suitable mill, affording wettable powders which can be diluted with water to give suspensions of the desired concentration.

| (b) Emulsifiable concentrate | |
|---|---|
| active ingredient | 10% |
| octylphenol polyethylene glycol ether (4-5 moles of ethylene oxide) | 3% |
| calcium dodecylbenzenesulfonate | 3% |
| castor oil polyglycol ether (36 moles of ethylene oxide) | 4% |
| cyclohexanone | 30% |
| xylene mixture | 50%. |

Emulsions of any required concentration can be obtained from this concentrate by dilution with water.

| (c) Dusts | (a) | (b) |
|---|---|---|
| active ingredient | 5% | 8% |
| talcum | 95% | — |
| kaolin | — | 92% |

Dusts which are ready for use are obtained by mixing the active ingredient with the carriers, and grinding the mixture in a suitable mill.

| (d) Extruder granulate | |
|---|---|
| active ingredient | 10% |
| sodium lignosulfonate | 2% |
| carboxymethylcellulose | 1% |
| kaolin | 87%. |

The active ingredient is mixed and ground with the adjuvants, and the mixture is subsequently moistened with water. The mixture is extruded and then dried in a stream of air.

| (e) Coated granulate | |
|---|---|
| active ingredient | 3% |
| polyethylene glycol 200 | 3% |
| kaolin | 94%. |

The finely ground active ingredient is uniformly applied, in a mixer, to the kaolin moistened with polyethylene glycol. Non-dusty coated granulates are obtained in this manner.

| (f) Suspension concentrate | |
|---|---|
| active ingredient | 40% |
| ethylene glycol | 10% |
| nonylphenol polyethylene glycol ether (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32%. |

The finely ground active ingredient is intimately mixed with the adjuvants, giving a suspension concentrate from which suspensions of any desired concentration can be obtained by dilution with water.

BIOLOGICAL EXAMPLES

Example 4:

Preemergence herbicidal action

In a greenhouse, immediately after sowing the test plants in seed dishes, the surface of the soil is treated with an aqueous dispersion of test compound, obtained from a 25% emulsifiable concentrate or from a 25% wettable powder with active ingredients which, on account of their insufficient solubility, cannot be processed to an emulsifiable concentrate. The seed dishes are kept in the greenhouse at 22°-25° C. and 50-70% relative humidity, and the test is evaluated after 3 weeks.

In this test the compounds of formula exhibit excellent herbicidal action against monocot weeds and some dicot weeds, whilst the growth of cultivated dicot plants is not affected or affected only insignificantly at higher rates of application.

| | Preemergence herbicidal action | | | | | |
|---|---|---|---|---|---|---|
| Compound kg a.i./ha | Compound 3 | | Compound 5 | | Compound 7 | |
| Test plant | 4 kg | 2 kg | 4 kg | 2 kg | 4 kg | 2 kg |
| Alopecurus myos. | 2 | 2 | 1 | 1 | 1 | 1 |
| Avena fatua | 6 | — | 2 | — | 5 | — |
| Echinochloa c.g. | 1 | 1 | 1 | 1 | 1 | 1 |
| Rottboellia ex. | 1 | 2 | 1 | 1 | 1 | 1 |

| | Preemergence herbicidal action | | | | | |
|---|---|---|---|---|---|---|
| Compound kg a.i./ha | Compound 3 | | Compound 5 | | Compound 7 | |
| Test plant | 4 kg | 2 kg | 4 kg | 2 kg | 4 kg | 2 kg |
| *Setaria ital.* | 1 | — | 1 | — | 1 | — |
| soybeans | 9 | 9 | 9 | 9 | 9 | 9 |
| cotton | 9 | 9 | 9 | 9 | 9 | 9 |
| sugar beet | 9 | 9 | 9 | 9 | 9 | 9 |
| *Sinapis alba* | 9 | — | 6 | — | 9 | — |
| *Stellaria med.* | 7 | — | 9 | — | 9 | — |

Example 5:

Postemergence herbicidal action (contact herbicide)

One or more weeds and cultivated plants, both monocots and dicots, are sprayed postemergence, in the 4- to 6-leaf stage, with a dispersion of active ingredient at different concentrations and then kept at 23°–26° C. and 45–60% relative humidity. The test is evaluated 15 days after treatment.

In this test too the compounds of formula I prove to be excellent selective herbicides. Cultivated dicot plants are not damaged or damaged only at higher rates of application.

| | Postemergence herbicidal action | | | | | |
|---|---|---|---|---|---|---|
| Compound kg a.i./ha | Compound 3 | | Compound 5 | | Compound 7 | |
| Test plant | 1 kg | 0,5 kg | 1 kg | 0,5 kg | 1 kg | 0,5 kg |
| *Avena fatua* | 2 | 7 | 1 | 1 | 1 | 1 |
| *Alopecurus myos.* | 2 | 2 | 1 | 1 | 1 | 1 |
| *Echinochloa c.g.* | 1 | 1 | 1 | 1 | 1 | 1 |
| *Rottboellia ex.* | 1 | 2 | 1 | 1 | 1 | 1 |
| soybeans | 9 | 9 | 6 | 7 | 7 | 8 |
| cotton | 9 | 9 | 8 | 9 | 9 | 9 |
| sugar beet | 9 | 9 | 7 | 9 | 8 | 9 |

Example 6:

Promotion of root growth (a) Seed dressing: The compounds of formula I are sprayed as aqueous emulsion onto the seeds in rates of application of 13 mg a.i./kg of seed. 10 of the treated seeds are sown in each of a number of flat dishes filled with soil and kept in climatic chambers under controlled conditions. After 10 days, when the seeds have germinated, the seedlings are carefully washed out of the soil. The test is evaluated by determining the length and weight of the roots in comparison with seedlings reared from untreated seeds.

Results:

(% in comparison with untreated controls)
Test plant: wheat
active ingredient: compound 3

| Length of root | | Weight of root | |
|---|---|---|---|
| cm | % in comparison with control | mg | % in comparison with control |
| 12.0 | 145 | 48 | 41 |

(b) Soil treatment:

Immediately after 10 seeds have been sown in each of a number of flat dishes filled with soil, the active ingredients are sprayed in concentrations of 0.3 and 1 kg a.I./ha onto the surface of the soil. The dishes are then kept in climatic chambers under controlled conditions. Evaluation of the test is made 10 days later using the same criteria as in (a).

Results:

(% in comparison with untreated controls)
Test plant: wheat
active ingredient: compound 3

| | Length of root | | Weight of root | |
|---|---|---|---|---|
| Rate of application | cm | % in comparison with control | mg | % in comparison with control |
| 0.3 kg a.i./ha | 13.0 | 163 | 124 | 115 |
| 1.0 kg a.i./ha | 10.0 | 125 | 98 | 91 |

What is claimed is:

1. A 2-[4-(6-Haloquinoxalinyl-2-oxy)phenoxy]propionic acid ester of the general formula I

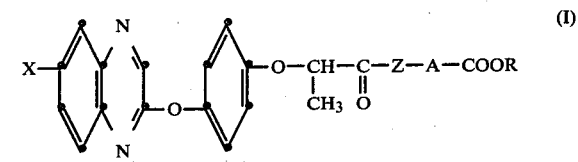

wherein X is fluorine, chlorine or bromine, Z is oxygen or sulfur, A is a $C_1$–$C_4$alkylene bridge which is unsubstituted or substituted by methyl or ethyl, and R is $C_1$–$C_4$alkyl.

2. A compound of the formula I according to claim 1, wherein X is fluorine or chlorine.

3. A compound of the formula I according to claim 1, wherein A is a $C_1$–$C_2$alkylene bridge which is unsubstituted or substituted by methyl or ethyl and which contains altogether at most 3 carbon atoms.

4. A compound of the formula I according to either of claims 2 or 3, wherein X is fluorine or chlorine and A is a $C_1$–$C_2$alkylene bridge which is unsubstituted or substituted by methyl or ethyl and which contains altogether at most 3 carbon atoms.

5. Methoxycarbonylmethyl 2-[4-(6-chloroquinoxalinyl-2-oxy)phenoxy]thiopropionate according to claim 1.

6. 1-(Ethoxycarbonyl)-n-propyl 2-[4-(6-chloroquinoxalinyl-2-oxy)-phenoxy]propionate according to claim 1.

7. 1-(n-Butoxycarbonyl)ethyl 2-[4-(6-chloroquinoxalinyl-2-oxy)-phenoxy]propionate according to claim 1.

8. Ethoxycarbonylmethyl 2-[4-(6-fluoroquinoxalinyl-2-oxy)phenoxy]propionate according to claim 1.

9. Methoxycarbonylmethyl 2-[4-(6-fluoroquinoxalinyl-2-oxy)-phenoxy]thiopropionate according to claim 1.

10. 1-(Methoxycarbonyl)ethyl 2-[4-(6-fluoroquinoxalinyl-2-oxy)-phenoxy]propionate according to claim 1.

11. n-Butoxycarbonylmethyl 2-[4-(6-fluoroquinoxalinyl-2-oxy)-phenoxy]thiopropionate according to claim 1.

12. A herbicidal and plant growth regulating composition which contains at least one compound according to claim 1, together with an agriculturally suitable carrier thereof.

13. A method of controlling unwanted plant growth which comprises treating the unwanted plants or the locus thereof with a herbicidally effective amount of a compound of the formula I according to claim 1.

14. A method according to claim 13 for the selective control of monocot weeds in crops of cultivated plants.

15. A method according to either of claims 13 or 14, wherein the compound is applied postemergence.

16. A method of influencing plant growth which comprises treating the plants to be influenced or the locus thereof with a herbicidally effective amount of a compound of the formula I according to claim 1.

17. A method according to claim 16 of stimulating the root growth of cereals.

18. A method according to either of claims 16 or 17 which is carried out preemergence.

19. A method according to claim 17 which comprises treating seeds with active ingredient before sowing.

* * * * *